(12) United States Patent
Kirschman

(10) Patent No.: US 8,029,539 B2
(45) Date of Patent: Oct. 4, 2011

(54) OFFSET MULTIAXIAL OR POLYAXIAL SCREW, SYSTEM AND ASSEMBLY

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 802 days.

(21) Appl. No.: 11/960,119

(22) Filed: Dec. 19, 2007

(65) Prior Publication Data

US 2009/0163961 A1 Jun. 25, 2009

(51) Int. Cl.
*A61B 17/70* (2006.01)
(52) U.S. Cl. ........................................ 606/246
(58) Field of Classification Search .................. 606/246, 606/247–266, 267–279; 411/398; 280/86.753
See application file for complete search history.

(56) References Cited

U.S. PATENT DOCUMENTS

| | | |
|---|---|---|
| 483,342 A | 9/1892 | Bolte |
| 900,717 A | 10/1908 | Edward |
| 2,344,381 A | 3/1944 | Young |
| 3,019,504 A | 2/1962 | Castagliuolo |
| 3,648,691 A | 3/1972 | Lumb et al. |
| 3,752,203 A | 8/1973 | Hill, Jr. |
| 3,875,936 A | 4/1975 | Volz |
| 4,011,602 A | 3/1977 | Rybicki et al. |
| 4,085,744 A | 4/1978 | Lewis et al. |
| 4,269,178 A | 5/1981 | Keene |
| 4,289,124 A | 9/1981 | Zickel |
| 4,294,300 A | 10/1981 | Bouwman |
| 4,309,139 A | 1/1982 | Nakae |
| 4,411,259 A | 10/1983 | Drummond |
| 4,604,995 A | 8/1986 | Stephens et al. |
| 4,611,580 A | 9/1986 | Wu |
| 4,611,581 A | 9/1986 | Steffee |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,763,644 A | 8/1988 | Webb |
| 4,771,767 A | 9/1988 | Steffee |

(Continued)

FOREIGN PATENT DOCUMENTS

DE 3219575 A1 12/1983

(Continued)

OTHER PUBLICATIONS

Expedium Spine System, DePuy Spine; Aug. 2004; Raynham, MA 02767.

*Primary Examiner* — Eduardo C Robert
*Assistant Examiner* — Summer L. Kostelnik
(74) *Attorney, Agent, or Firm* — Jacox, Meckstroth & Jenkins

(57) ABSTRACT

A capless multiaxial screw fixation assembly, including: a screw having a threaded portion and a screw head portion positioned at one end thereof; and, a retainer having a first end, a second end opposite the first end, and a bore for receiving the screw threaded portion so that the screw head portion is seated therein. At least one of the screw and the retainer is configured such that the retainer is able to pivot about the screw head portion in a non-symmetrical manner.

25 Claims, 16 Drawing Sheets

U.S. PATENT DOCUMENTS

| | | | |
|---|---|---|---|
| 4,805,602 A | 2/1989 | Puno et al. | |
| 4,815,453 A | 3/1989 | Cotrel | |
| 4,887,595 A | 12/1989 | Heinig et al. | |
| 4,887,596 A | 12/1989 | Sherman | |
| 4,913,134 A | 4/1990 | Luque | |
| 4,946,458 A | 8/1990 | Harms et al. | |
| 4,950,269 A | 8/1990 | Gaines | |
| 5,005,562 A | 4/1991 | Cotrel | |
| 5,024,213 A | 6/1991 | Asher et al. | |
| 5,042,982 A | 8/1991 | Harms et al. | |
| 5,067,955 A | 11/1991 | Cotrel | |
| 5,084,049 A | 1/1992 | Asher et al. | |
| 5,092,867 A | 3/1992 | Harms et al. | |
| 5,113,685 A | 5/1992 | Asher et al. | |
| 5,120,171 A | 6/1992 | Lasner | |
| 5,127,912 A | 7/1992 | Ray et al. | |
| 5,129,900 A | 7/1992 | Asher et al. | |
| 5,176,680 A | 1/1993 | Vignaud et al. | |
| 5,183,359 A | 2/1993 | Barth | |
| 5,190,543 A | 3/1993 | Schlapfer | |
| 5,207,678 A | 5/1993 | Harms et al. | |
| 5,261,913 A | 11/1993 | Marnay | |
| 5,360,431 A | 11/1994 | Puno et al. | |
| 5,380,325 A | 1/1995 | Lahille et al. | |
| 5,466,237 A | 11/1995 | Byrd et al. | |
| 5,474,555 A | 12/1995 | Puno et al. | |
| 5,624,442 A | 4/1997 | Mellinger et al. | |
| 5,702,486 A * | 12/1997 | Craig et al. | 623/19.14 |
| 5,797,911 A | 8/1998 | Sherman et al. | |
| 5,879,350 A | 3/1999 | Sherman et al. | |
| 5,885,286 A | 3/1999 | Sherman et al. | |
| 5,891,145 A | 4/1999 | Morrison et al. | |
| 6,660,004 B2 | 12/2003 | Barker et al. | |
| 6,755,829 B1 | 6/2004 | Bono et al. | |
| 6,869,433 B2 | 3/2005 | Glascott | |
| 7,081,117 B2 | 7/2006 | Bono et al. | |
| 7,125,426 B2 | 10/2006 | Moumene et al. | |
| 2002/0120272 A1 | 8/2002 | Yuan et al. | |
| 2004/0225289 A1* | 11/2004 | Biedermann et al. | 606/61 |
| 2005/0033296 A1 | 2/2005 | Bono et al. | |
| 2005/0177154 A1 | 8/2005 | Moumene et al. | |
| 2006/0058788 A1* | 3/2006 | Hammer et al. | 606/61 |
| 2006/0155278 A1 | 7/2006 | Warnick | |
| 2006/0161152 A1 | 7/2006 | Ensign et al. | |
| 2006/0161153 A1 | 7/2006 | Hawkes et al. | |
| 2006/0173456 A1 | 8/2006 | Hawkes et al. | |
| 2006/0195086 A1 | 8/2006 | Sybert | |
| 2006/0235393 A1 | 10/2006 | Bono et al. | |
| 2007/0043357 A1* | 2/2007 | Kirschman | 606/61 |
| 2007/0053765 A1 | 3/2007 | Warnick et al. | |
| 2007/0093826 A1 | 4/2007 | Hawkes et al. | |
| 2007/0093827 A1 | 4/2007 | Warnick | |
| 2007/0123862 A1 | 5/2007 | Warnick | |

FOREIGN PATENT DOCUMENTS

| | | |
|---|---|---|
| DE | 3639810 A1 | 5/1988 |
| DE | 3711013 C1 | 6/1988 |
| DE | 9403231 U1 | 4/1994 |
| EP | 128058 A1 | 12/1984 |
| EP | 242705 A2 | 10/1987 |
| EP | 242708 A2 | 10/1987 |
| EP | 1190678 A2 | 3/2002 |
| FR | 2615095 A1 | 11/1988 |
| FR | 2624720 A1 | 6/1989 |
| FR | 2852815 A1 | 10/2004 |
| GB | 167228 | 7/1921 |
| GB | 2173104 A | 10/1986 |
| WO | 8707134 A1 | 12/1987 |
| WO | 01/52758 A1 | 7/2001 |
| WO | 2006/047555 A2 | 5/2006 |
| WO | 2006/047707 A2 | 5/2006 |
| WO | 2006/047711 A2 | 5/2006 |

* cited by examiner

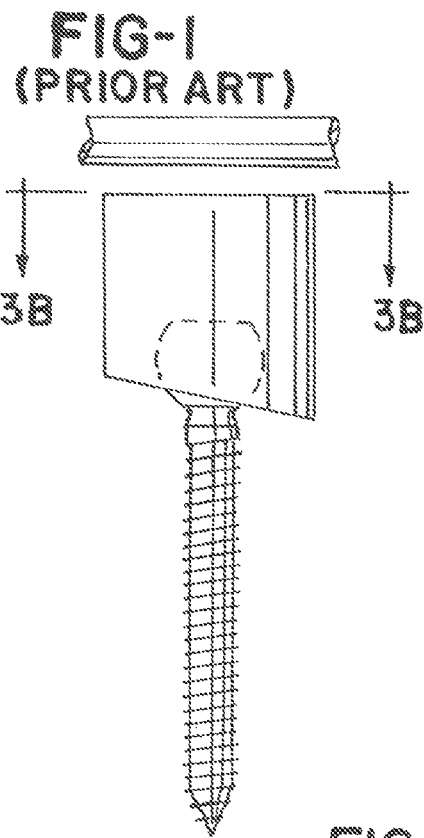
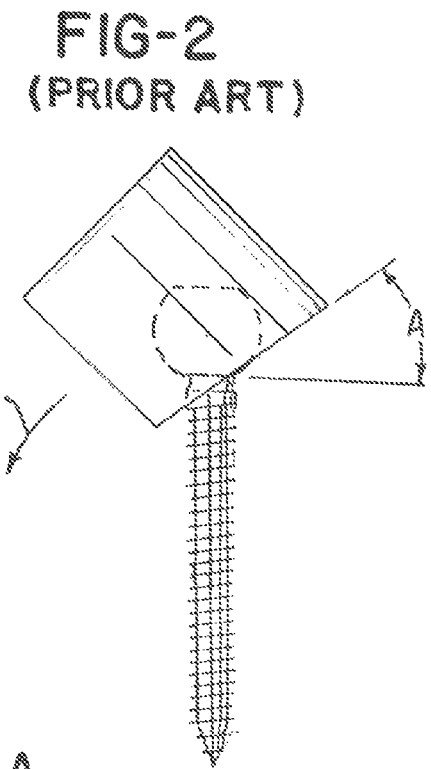
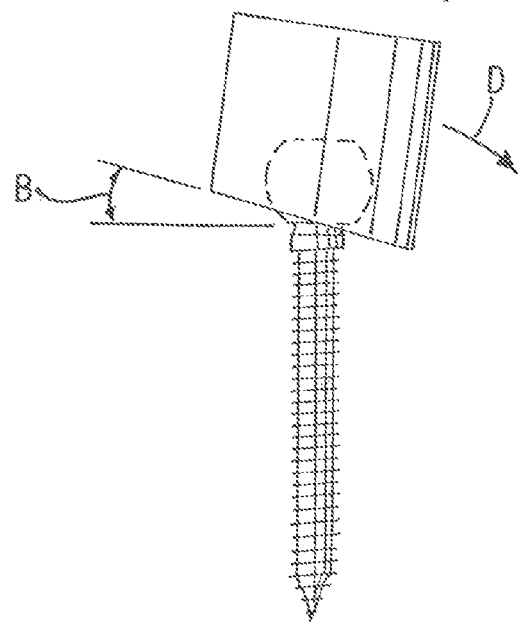
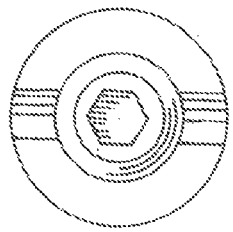

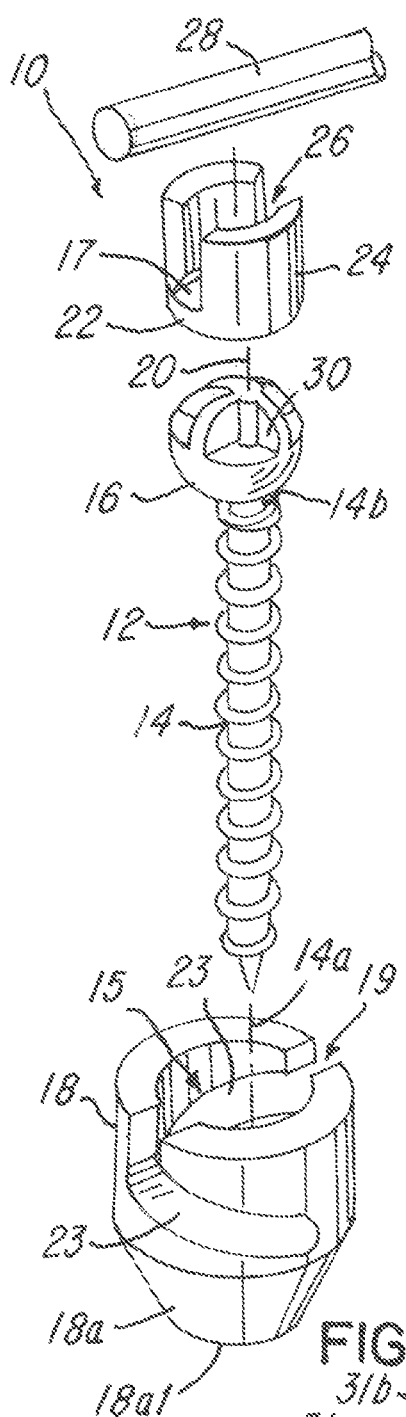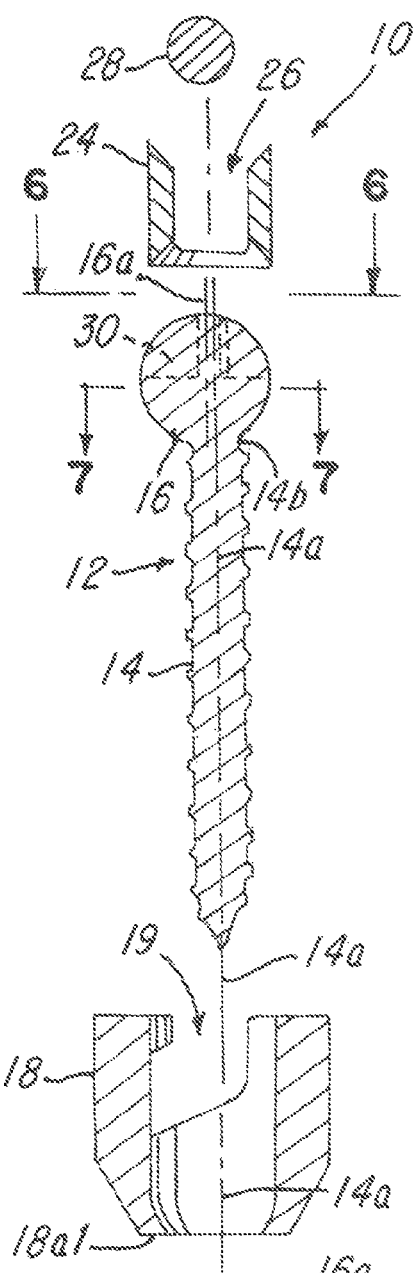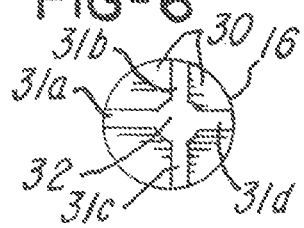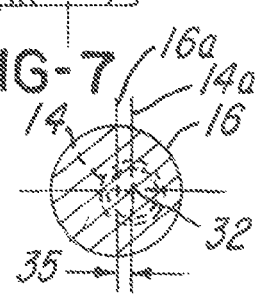

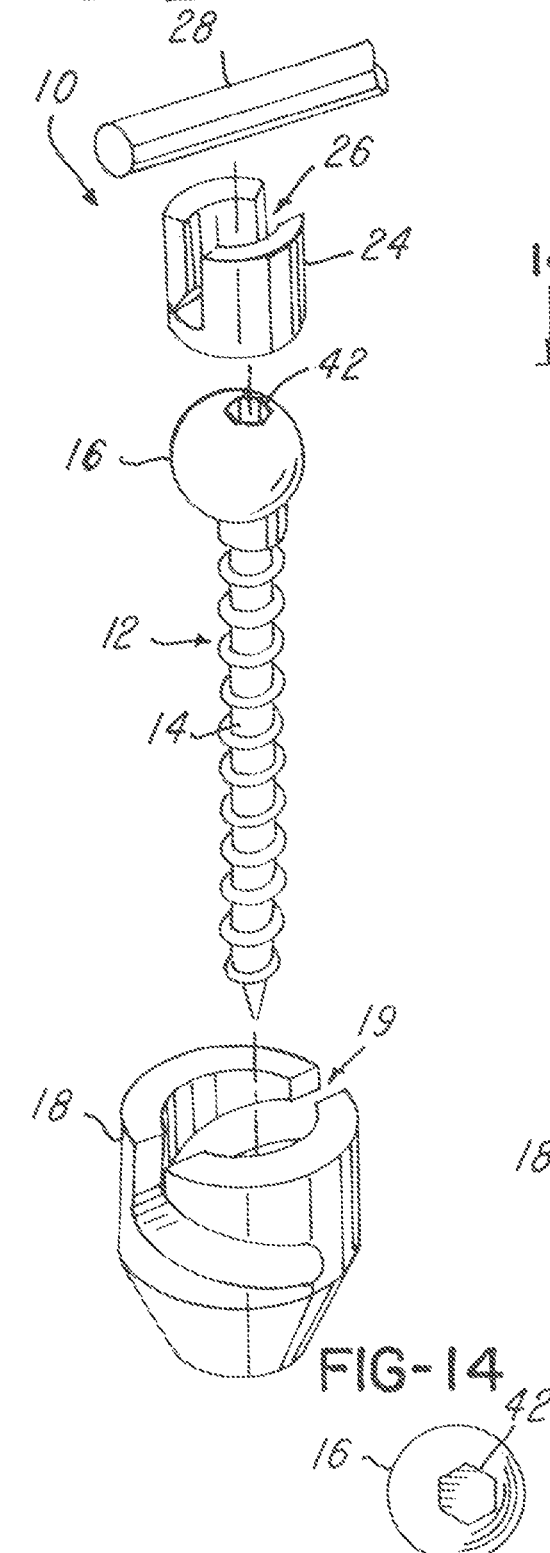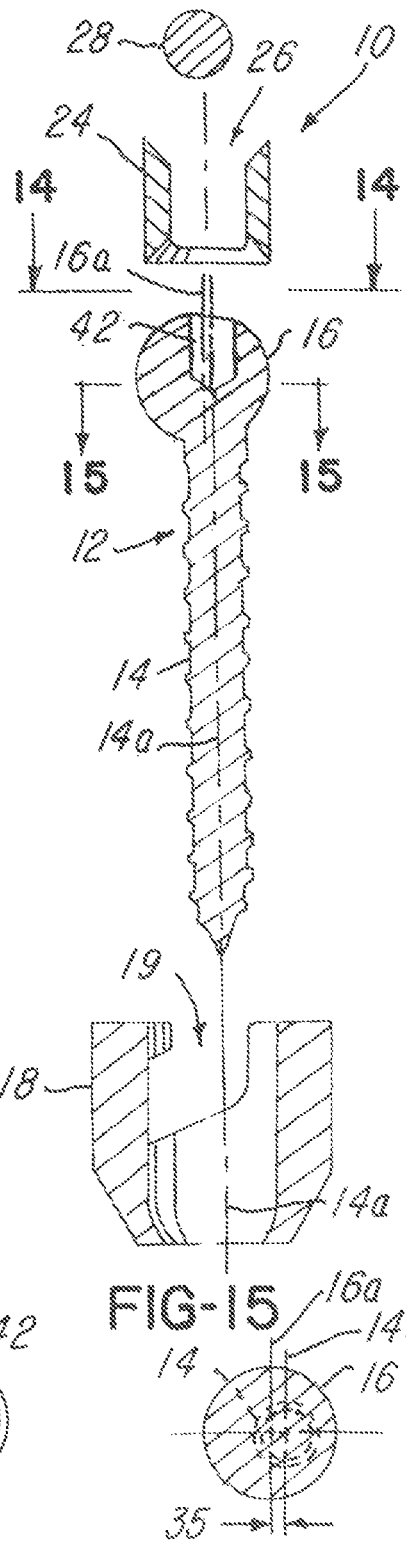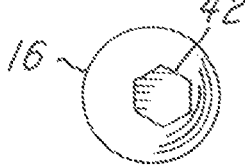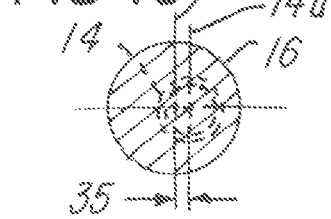

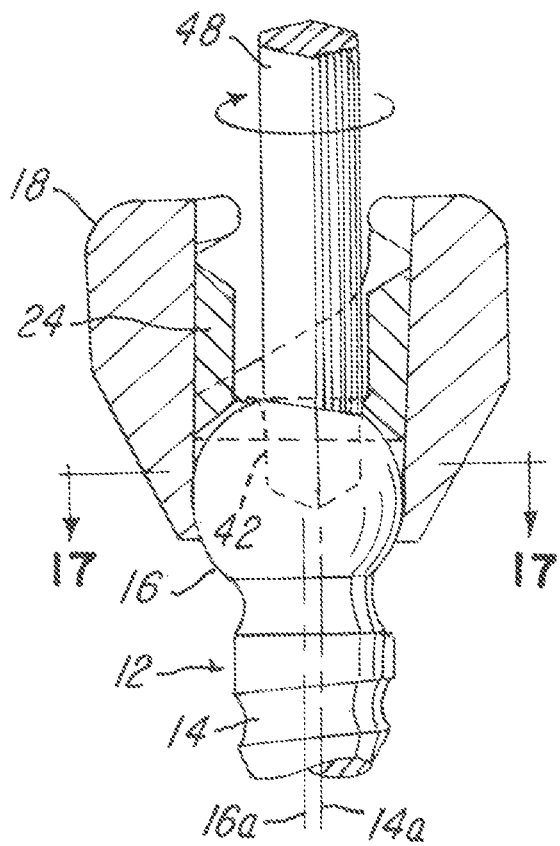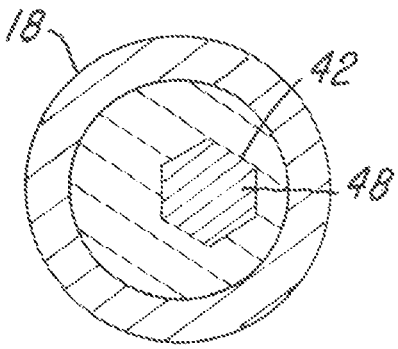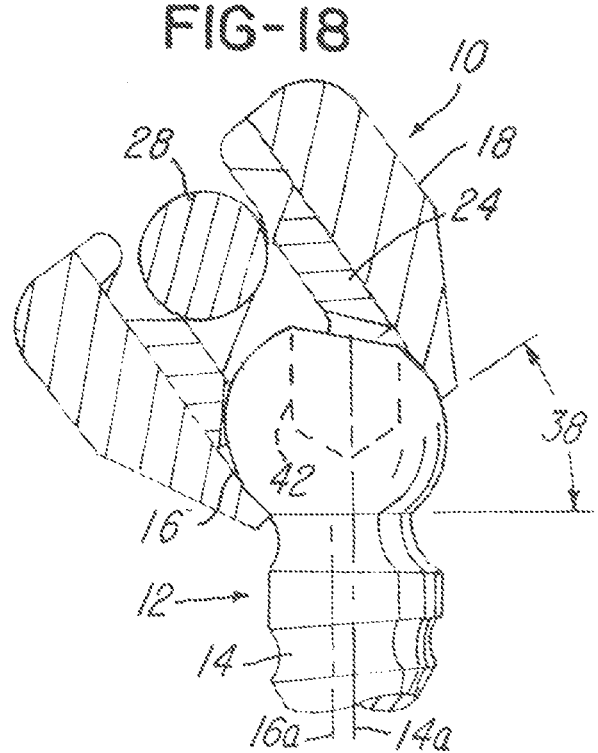

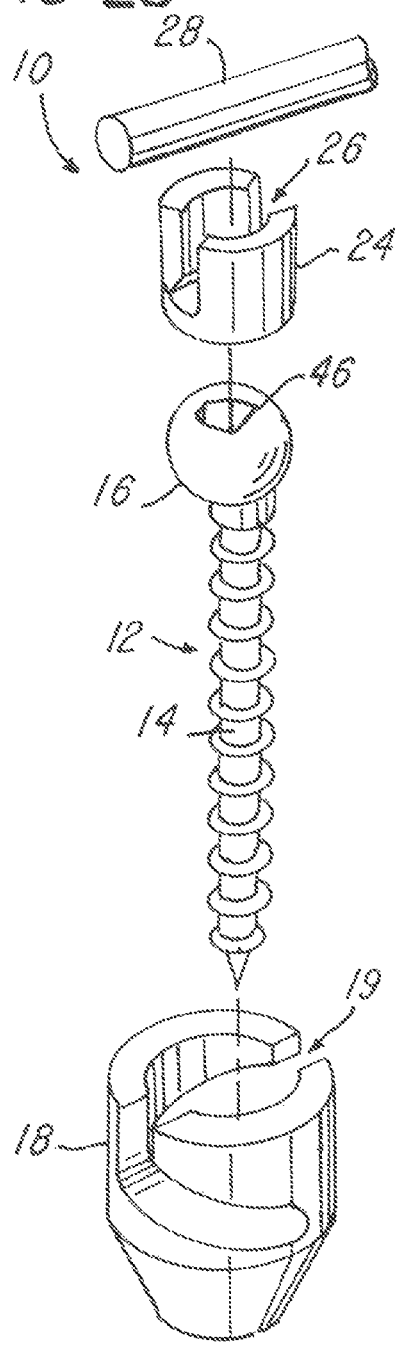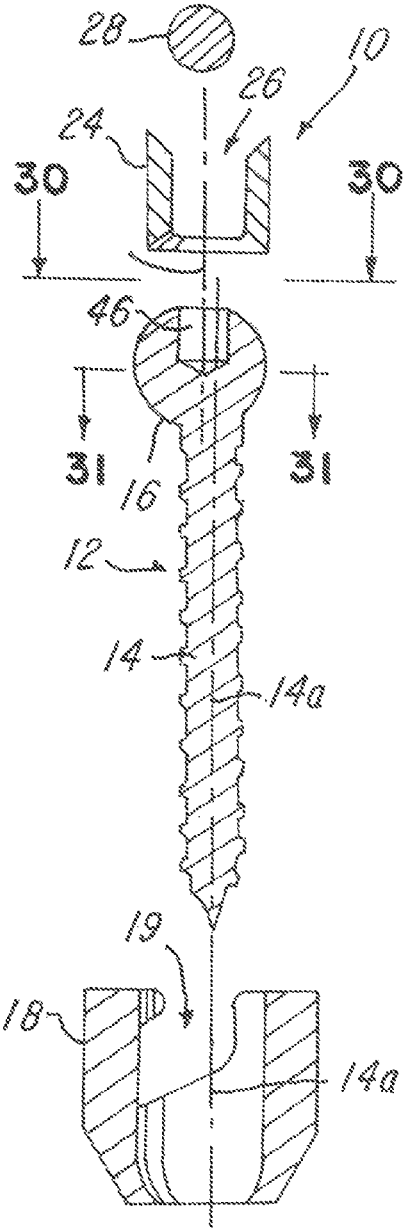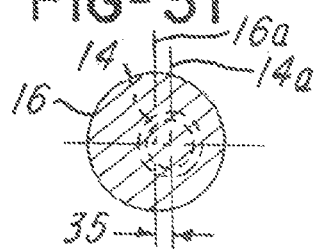

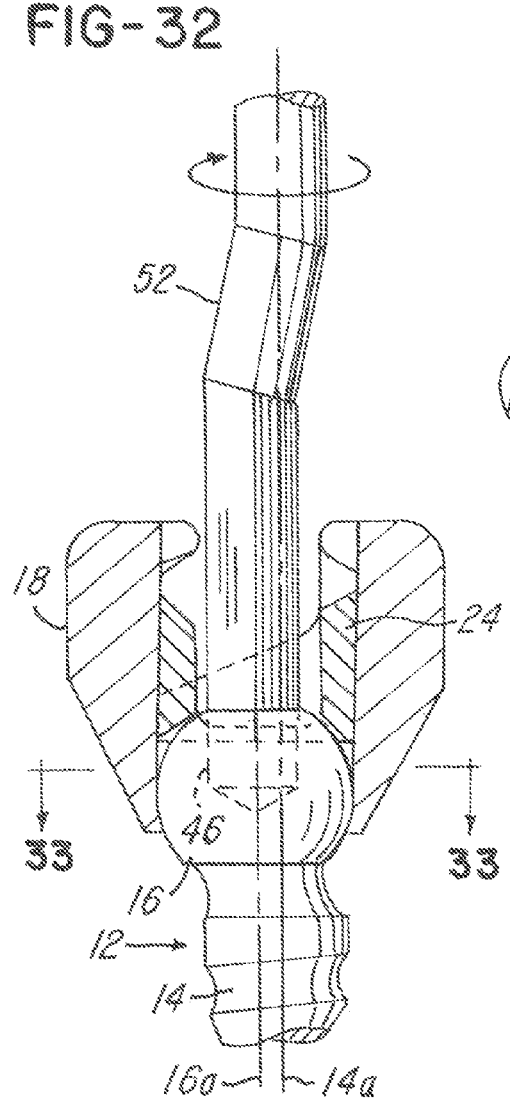
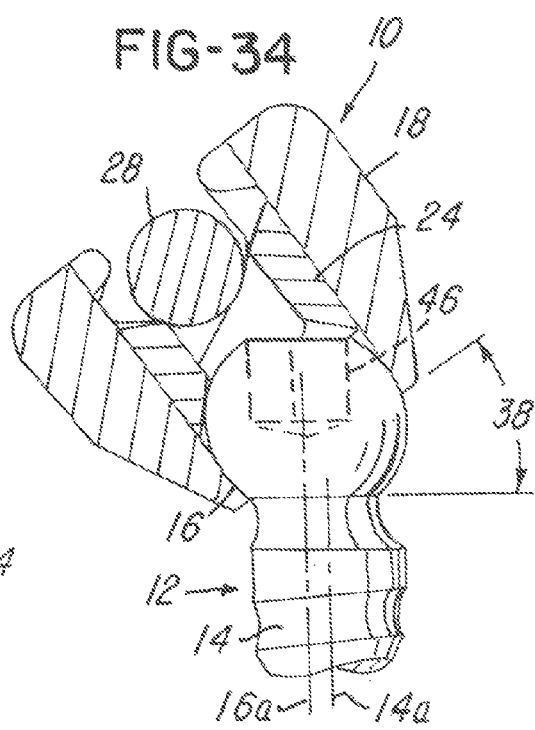
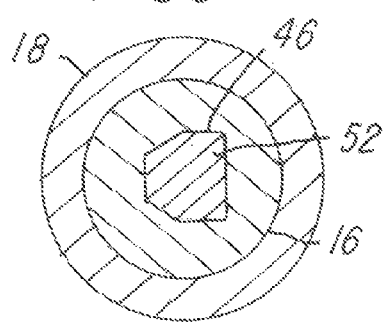
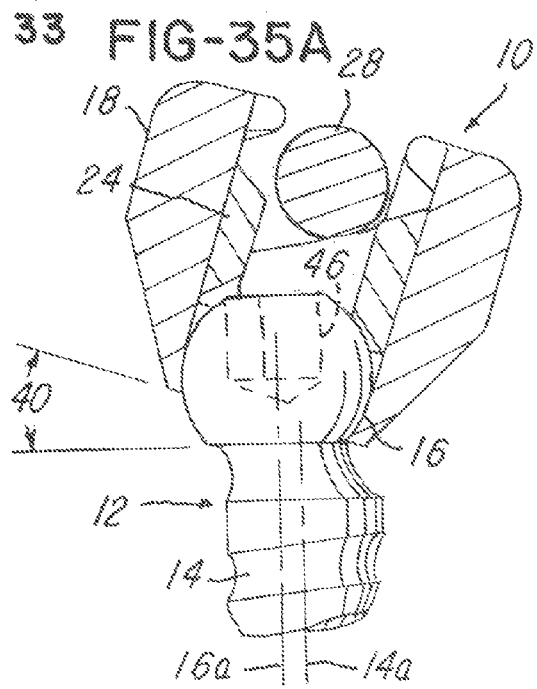

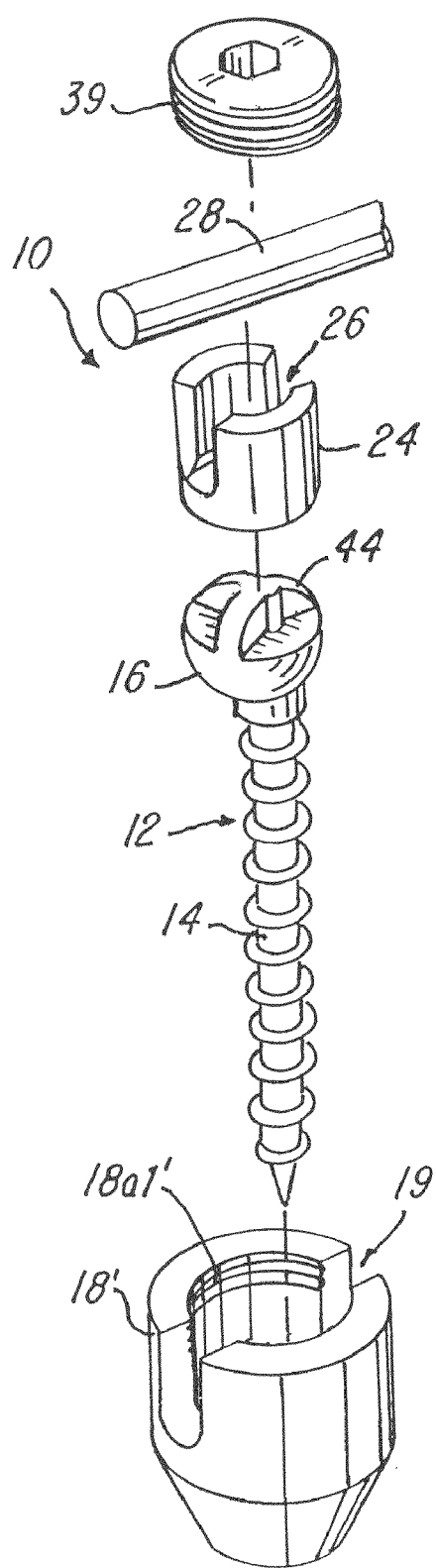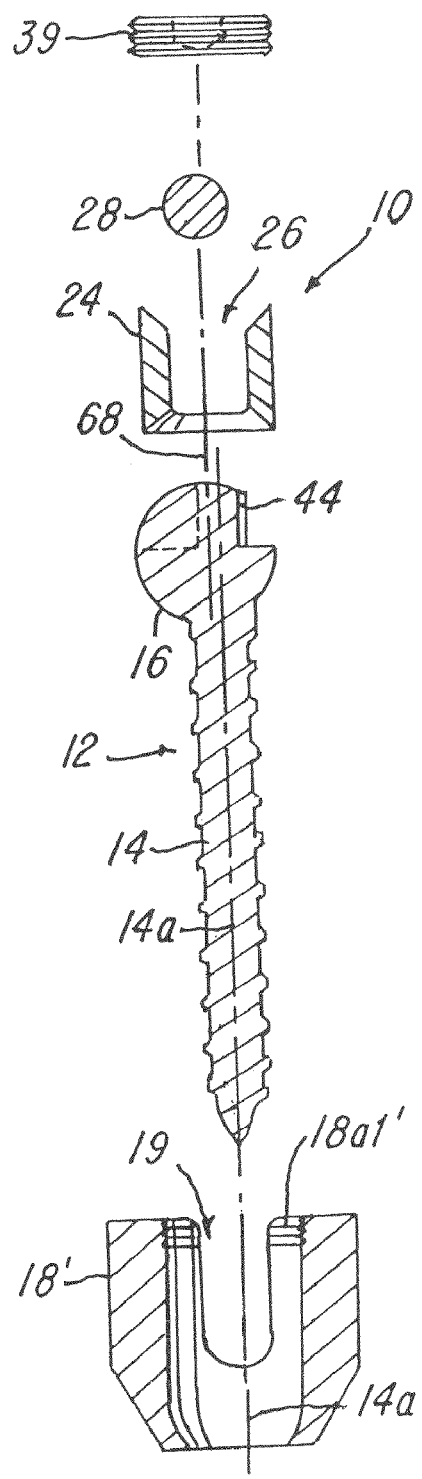

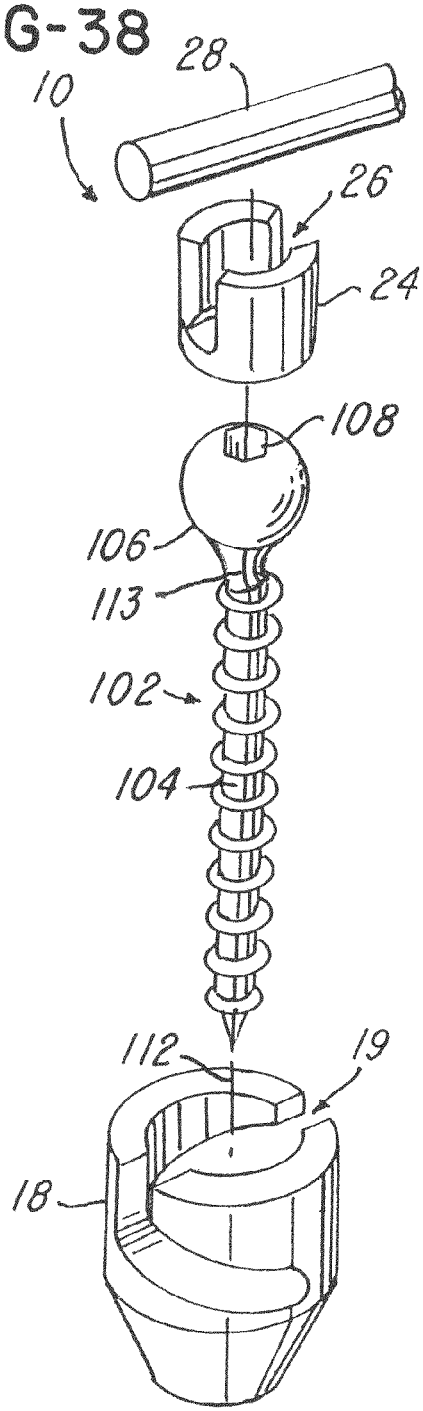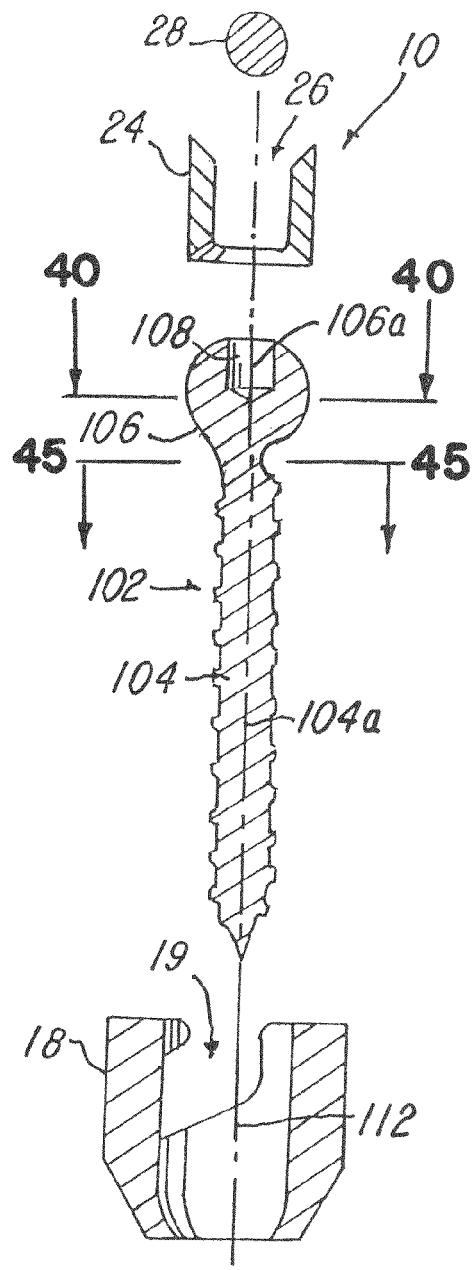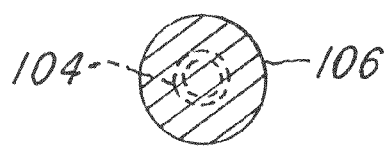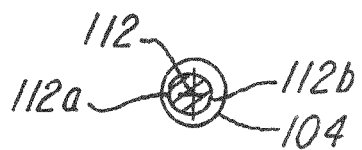

OFFSET MULTIAXIAL OR POLYAXIAL SCREW, SYSTEM AND ASSEMBLY

BACKGROUND OF THE INVENTION

1. Field of the Invention

The present invention relates generally to a screw having an offset head and to a multiaxial or polyaxial screw for use with a bone fixation system and, in particular, to a multiaxial or polyaxial screw which permits a greater range of pivotability in at least one direction.

2. Description of the Related Art

As is generally known in the art, spinal abnormalities may be correctable using a pair of posterior spinal fixation rods attached to the vertebrae using pedicle screws and the like. In order to provide increased stability and rigidity, especially to resist twisting or the like, the pair of elongated rods often include cross connecting devices. The cross connecting devices typically traverse the spinal column and couple to each of the elongated rods. In other words, the cross connecting devices are perpendicular or substantially perpendicular to the spinal column.

In addition, bone screws with a polyaxial head are commonly used in spine surgery today. They are used chiefly in the lumbar spine and screwed into bone (pedicle) posteriorly. The head of the screw is attached to the shaft of the screw. The head of the screw is machined into a ball, and the head may be provided with a receiver or socket into which the ball fits. One typical prior art system further contains a receiver for receiving a separate rod. The rod is fastened to the screw head receiver via a threaded cap. The rod is then fastened to screws placed in adjacent vertebrae thus providing stabilization. The polyaxial head allows the rod to be placed in a variety of angles with respect to the screw allowing conformance to local anatomy.

Exemplary bone screws are disclosed in the following patents: U.S. Pat. No. 5,466,237 to Bird et al.; U.S. Pat. No. 4,946,458 to Harms; U.S. Pat. No. 5,207,678 to Harms et al.; U.S. Pat. No. 5,474,555 to Puno et al.; and U.S. Pat. No. 6,869,433 to Glascott. It will be appreciated from the prior art, however, that multiaxial screws involve the ability to pivot symmetrically or the same amount in each direction. In some instances, it is desired for the retainer to be moved or pivoted about the screw head more in a certain direction than in another, whereby greater maneuverability of the rod attached to the retainer may be accommodated. It was difficult to get a "favorable angle" of the retainer relative to the screw head.

FIGS. 1-3B show a prior art system wherein a retainer having an angled or canted surface that permits movement between a predetermined angle A (FIG. 2) and a different smaller angle B (FIG. 3A) when the retainer is moved between a first direction C and a second direction D, respectively.

Thus, it would be desirable for a multiaxial screw assembly to be developed for use with a spinal fixation system which permits non-symmetrical pivoting and that is capable of use with a variety of retainers, including those with non-canted surfaces. It would also be desirable for a multiaxial screw assembly to be developed in which simple modification of existing components enables the desired pivoting action.

SUMMARY OF THE INVENTION

It is therefore, an object of the invention to provide a polyaxial screw having a head that provides a greater range of mobility.

In one aspect, one embodiment comprises a multiaxial screw fixation assembly, comprising a screw having a threaded portion and a screw head portion positioned at one end thereof, and a retainer having a first end, a second end opposite said first end, and a bore for receiving said threaded portion so that said screw head portion may be seated therein, wherein said screw is adapted such that said retainer is able to pivot about said screw head portion in a non-symmetrical manner.

In another aspect, another embodiment comprises a multiaxial screw fixation assembly, comprising a screw, further comprising a threaded portion having a centerline axis extending therethrough, and a head portion positioned at one end of said threaded portion, said head portion having a centerline axis extending therethrough, wherein said screw head portion is not aligned with said screw threaded portion, and a retainer having a first end, a second end opposite said first end, a centerline axis extending therethrough, and a bore for receiving said screw threaded portion so that said screw head portion is seated therein axis, wherein said retainer is able to pivot about said screw head portion in a non-symmetrical manner.

In still another aspect, another embodiment comprises a retainer for use in a spinal fixation procedure, said retainer comprising a retainer body having a first end for receiving a rod, said retainer also comprising a bore for receiving a shank of a screw having a screw head, said retainer body having a second end adapted to permit said retainer to pivot or move in a first direction a first predetermined angle and further adapted to permit the retainer to pivot or move in a second direction a second predetermined angle, wherein said second predetermined angle is less than said first predetermined angle.

In yet another aspect, another embodiment comprises a polyaxial screw for use during a spinal procedure, said polyaxial screw comprising a threaded shank having a shank axis, and a head integral with said threaded shank, said head being adapted to permit a retainer to pivot or move about a head axis, said head axis being offset from said shank axis.

These and other objects and advantages of the invention will be apparent from the following description, the accompanying drawings and the appended claims.

BRIEF DESCRIPTION OF THE OF THE ACCOMPANYING DRAWINGS

FIG. 1 is a front elevation view of a prior art retainer having a centered bottom edge;

FIG. 2 is a front elevation view of a prior art retainer, wherein the retainer associated therewith is shown in a first pivoted position;

FIG. 3A is a front elevation view of the prior art retainer assembly depicted in FIGS. 1 and 2, wherein the retainer associated therewith is shown in a second pivoted position;

FIG. 3B is a top view of the prior art retainer taken along the line 3B-3B in FIG. 1;

FIG. 4 is an exploded perspective view of the polyaxial screw assembly having an offset head, wherein a compression member and a rod for engagement with the compression member are also shown;

FIG. 5 is an exploded side view of the polyaxial screw assembly depicted in FIG. 4;

FIG. 6 is a top view of the polyaxial screw assembly depicted in FIGS. 4 and 5 taken along line 6-6 in FIG. 5;

FIG. 7 is a top sectional view of the polyaxial screw assembly depicted in FIGS. 4-6 taken along line 7-7 in FIG. 5;

FIG. 12 is an exploded perspective view of a polyaxial screw assembly having a first alternative configuration, wherein a compression member and a rod for engagement with the compression member are also shown;

FIG. 13 is an exploded side view of the polyaxial screw assembly depicted in FIG. 12;

FIG. 14 is a top view of the polyaxial screw assembly depicted in FIGS. 12 and 13 taken along line 14-14 in FIG. 13;

FIG. 15 is a top sectional view of the polyaxial screw assembly depicted in FIGS. 12 and 13 taken along line 15-15 in FIG. 13;

FIG. 16 is an enlarged, partial sectional view of the polyaxial screw assembly depicted in FIGS. 12 and 13, wherein a tool is shown as interfacing with a head portion thereof to position it within the retainer;

FIG. 17 is a top section view of the polyaxial screw assembly with the head portion thereof positioned within the retainer, as depicted in FIG. 26, taken along line 17-17 of FIG. 16;

FIG. 18 is an enlarged, partial sectional view of the polyaxial screw assembly depicted in FIG. 16, wherein the compression member and rod engaged therewith are included and the retainer has been pivoted to a maximum degree in a first direction;

FIG. 28 is an exploded perspective view of a polyaxial screw assembly having a third alternative configuration, wherein a compression member and a rod for engagement with the compression member are also shown;

FIG. 29 is an exploded side view of the polyaxial screw assembly depicted in FIG. 28;

FIG. 30 is a top view of the polyaxial screw assembly depicted in FIGS. 28 and 29 taken along line 30-30 in FIG. 29;

FIG. 31 is a top sectional view of the polyaxial screw assembly depicted in FIGS. 28 and 29 taken along line 31-31 in FIG. 29;

FIG. 32 is an enlarged, partial sectional view of the polyaxial screw assembly depicted in FIGS. 28 and 29, wherein a tool is shown as interfacing with a head portion thereof to position it within the retainer;

FIG. 33 is a top sectional view of the polyaxial screw assembly with the head portion thereof positioned within the retainer, as depicted in FIG. 32, taken along line 33-33 of FIG. 32;

FIG. 34 is an enlarged, partial sectional view of the polyaxial screw assembly depicted in FIG. 32, wherein the compression member and rod engaged therewith are included and the retainer has been pivoted to a maximum degree in a first direction;

FIGS. 35A and 35B are enlarged, partial sectional view of the polyaxial screw assembly depicted in FIG. 32, wherein the compression member and rod engaged therewith in unlocked and locked positions;

FIG. 36 is an exploded view of another embodiment of the invention illustrating the polyaxial screw assembly used in combination with a retainer that utilizes a cap, such as a thread cap;

FIG. 37 is a sectional exploded view of the embodiment shown in FIG. 36;

FIG. 38 is a view of another embodiment of the invention wherein a screw head has a common or coaxial axis with the shank;

FIG. 39 is a sectional view of the embodiment shown in FIG. 38;

FIG. 40 is a sectional view taken along the line 40-40 in FIG. 39;

FIG. 45 is a sectional view of an intermediate portion showing its eccentricity and non-symmetry about an axis.

DETAILED DESCRIPTION OF THE PREFERRED EMBODIMENTS

Figure 8:
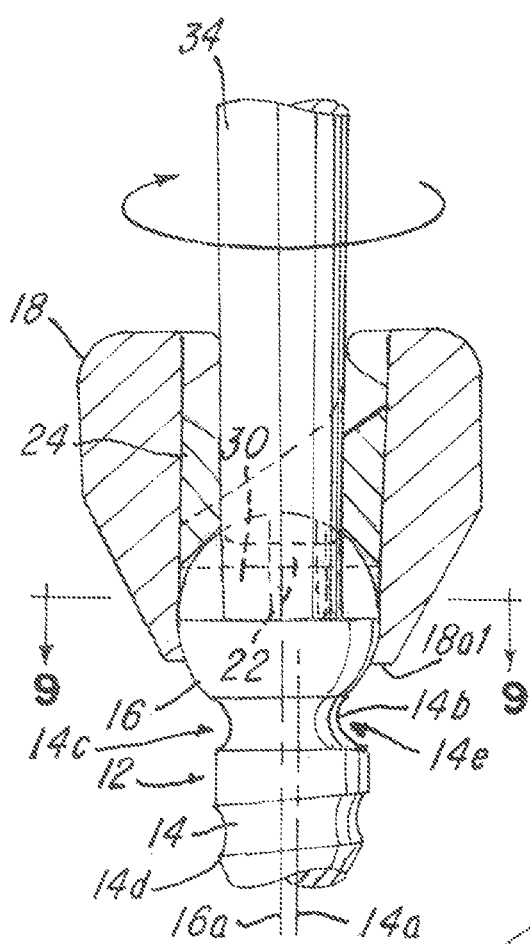
FIG. 8 is an enlarged, partial sectional view of the polyaxial screw assembly depicted in FIGS. 4 and 5, wherein a tool is shown as interfacing with a head portion thereof to position it within the retainer.

Referring now to the drawings in detail, wherein identical numerals indicate the same elements throughout the figures, FIGS. 4-35B depict various embodiments of a multi-axial screw and spinal fixation assembly 10. Spinal fixation assembly 10 includes a screw 12 having a threaded portion 14 and a screw head 16 that preferably has a rounded, arcuate, spherical or curved profile. Spinal fixation assembly 10 further includes a retainer 18, which preferably has a generally cylindrical configuration. In these illustrative embodiments, the retainer 18 is capless, but the retainer 18 could be non-capless, such as is illustrated in FIGS. 36 and 37 below. Although not shown, it will be appreciated that retainer 18 includes an aperture or bore 15 therethrough along a centerline axis 20 (FIG. 4). Accordingly, the bore 15 that receives a threaded portion 14 of the screw 12 until screw head 16 thereof is received adjacent a first end 18a of retainer 18. It will be understood that screw head 16 may be positioned within retainer 18 in any known manner so that multiaxial or polyaxial and relative movement between retainer 18 and screw 12 is permitted. In this way, a user, such as a surgeon or physician, is able to change the polyaxial position of retainer 18 relative to screw 12 in order to adjust an angular position of the retainer or receiving channel 19 and an elongated member or rod, such as rod 28 (FIG. 6), which is received and retained in the retainer 18 at a first end 18a.

Contrary to similar assemblies in the prior art shown in FIGS. 1-3B, screw 12 is configured so that the retainer 18 is able to pivot in a non-symmetrical manner about screw head 16. More specifically, it will be noted from the embodiment shown in FIGS. 10, 11A-11B, 18, 19A-19B, 26, 27A-27B, 34 and 35A-35B, that a centerline axis 16a of screw head 16 is offset from a centerline axis 14a of the threaded portion 14. The screw head 16 enables the retainer 18 to pivot by varying degrees in different directions. In this way, implementation of spinal fixation assembly 10 will permit a greater degree of movement of the retainer 18 toward the threaded portion 14, which may be desirable for a given application or case.

In the illustration, the retainer 18 which preferably has a generally cylindrical configuration with helical rod-receiving channels 21 and 23 (FIG. 4) similar to that described in detail in U.S. Patent Application Publication 2007/0043357 A1 to Kirschman U.S. patent application Ser. No. 11/193,523 filed Jul. 29, 2005; U.S. patent application Ser. No. 11/610,698 filed Dec. 14, 2006; and U.S. patent application Ser. No. 11/762,911 filed Jun. 14, 2007, which are also owned by the assignee of the present application and all of which are incorporated by reference and made a part hereof.

It will be appreciated that retainer 18 preferably includes a receiving channel 19 in communication with the helical rod-receiving channels 21 and 23 for engaging an elongated rod or member 28. In one embodiment, the rod 28 may engage directly against the screw head 16.

The spinal fixation assembly 10 may further include a compression member 24 that is received in the bore 15. The compression member 24 comprises a receiving channel 26 which is utilized to receive engage rod 28 and which engages the screw head 16.

As mentioned earlier, the screw 12 may be used with a non-capless retainer 18, such as retainer 18' in FIGS. 36 and 37, which utilizes a cap or other means for retaining rod 28 in the retainer.

While a centerline axis 14a through threaded portion 14 of screw 12 remains generally aligned with a centerline axis 16a through retainer 18, it will be appreciated that a centerline axis 16a through screw head 16, however, is generally offset from and not coaxial with centerline axes 14a and 16a. As such, screw head 16 may either be rotated so that centerline axis thereof is at a specified angle relative to centerline axes 14a and 16a or shifted in parallel to such centerline axes 14a and 16a. In either case, it will be understood that screw head 16 is not configured or oriented so as to be symmetrical with respect to or about the centerline axes 14a and 16a.

Screw head 16 preferably includes at least one female opening, slot or groove 30 (FIG. 4) so that a corresponding tool 34 is able to interact with screw 12 in order to threadingly screw the screw 12 into spinal bone. The opening 30 to be formed therein for receiving the corresponding tool 34 which enables screw 12 to be threaded into and out spinal bone. As best seen in FIGS. 6 and 9, the partial opening is configured as walls 31a, 31b, 31c and 31d that intersect at point 32 and that define recessed areas or slots 30 formed in screw head 16 (i.e., as for a Phillips screw). More specifically, the walls 31a, 31b, 31c and 31d define opening 30 in screw head 16. Note that the intersecting point 32 is aligned with centerline axis 14a of threaded portion 14 or a distance 35 (FIG. 7) from centerline axis 16a. In this way, the tool 34 (FIG. 8) is able to access the screw head 16 and slots 30 and pressure applied thereby is directed along centerline axis 14a.

Figure 9:
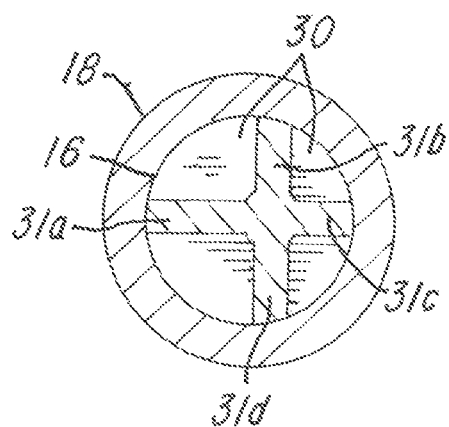
FIG. 9 is a top sectional view of the polyaxial screw assembly with the head portion thereof positioned within the retainer, as depicted in FIG. 8, taken along line 9-9 of FIG. 8.
Figure 10:
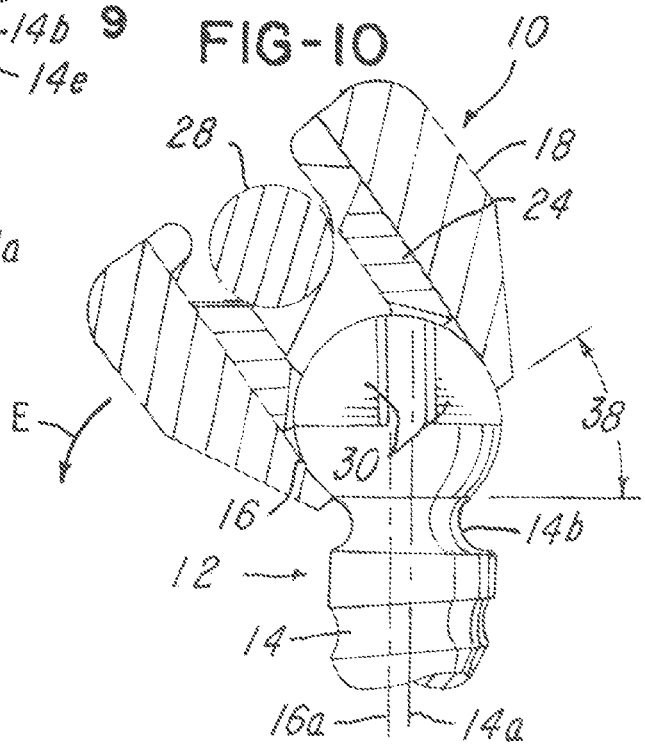
FIG. 10 is an enlarged, partial sectional view of the polyaxial screw assembly depicted in FIG. 8, wherein the compression member and rod engaged therewith are included and the retainer has been pivoted to a maximum degree in a first direction.
Figure 11A:
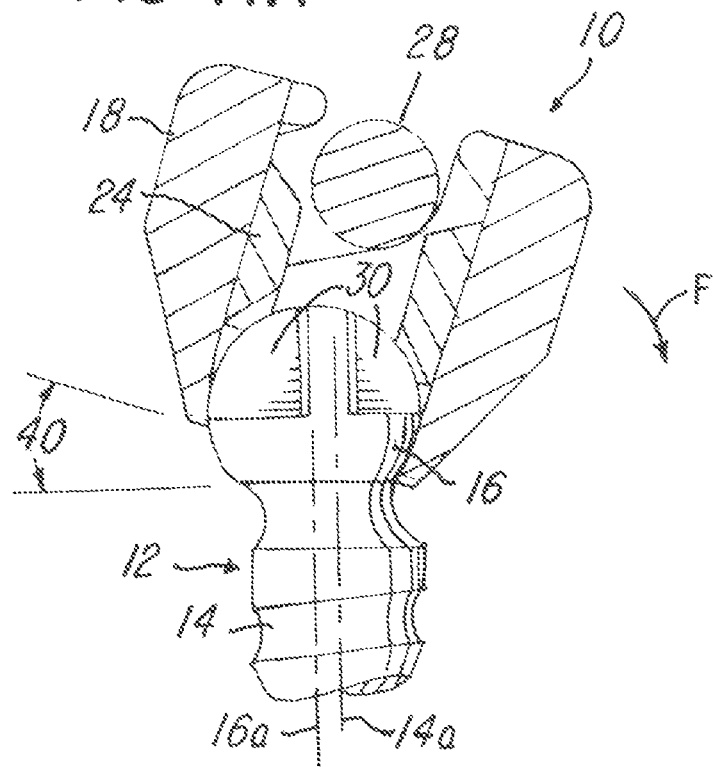
FIGS. 11A and 11B are enlarged, partial sectional views of the polyaxial screw assembly depicted in FIG. 8, wherein the compression member and rod in unlocked and locked positions and the retainer has been pivoted to a maximum degree in a second direction.

When screw head 16 is seated properly within retainer 18, as viewed for example in FIGS. 8, 10 and 11, it will be appreciated that the intentional misalignment of screw head 16 and threaded portion 14 creates the ability for retainer 18 (and compression member 24) to pivot non-symmetrically. For example, FIG. 10 depicts the pivoting of retainer 18 about screw head 16 in a first direction E as an angle 38 with a range of, for example, approximately 0°-55°. Similarly, FIG. 11A shows the pivoting of retainer 18 about screw head 16 in a second direction F (opposite the first direction), where an angle 40 has a range of, for example, approximately 0°-55°. Clearly, the maximum amount of movement or pivoting is greater in the first direction E than in the second direction F. This permits a desirable flexibility for the adjustment of rod 28 when secured as part of a spinal fixation assembly.

Figure 11B:
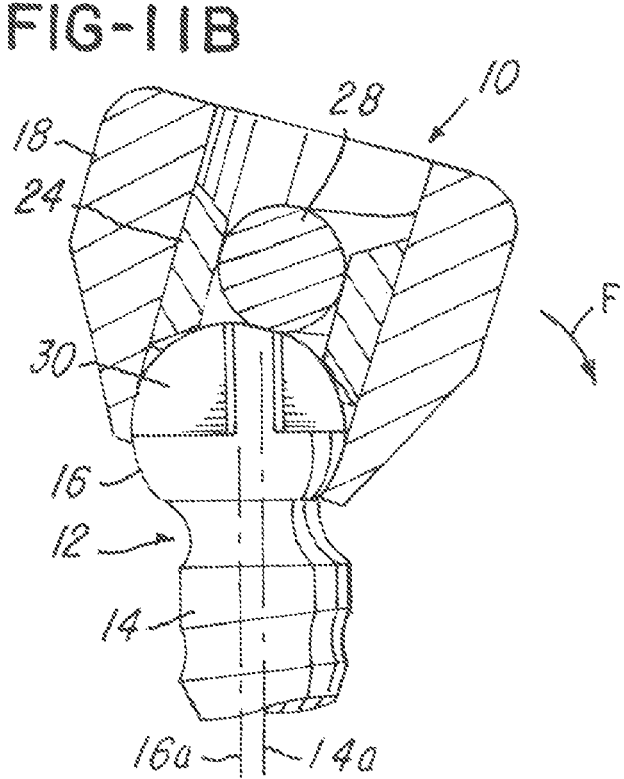
Figure 19A:
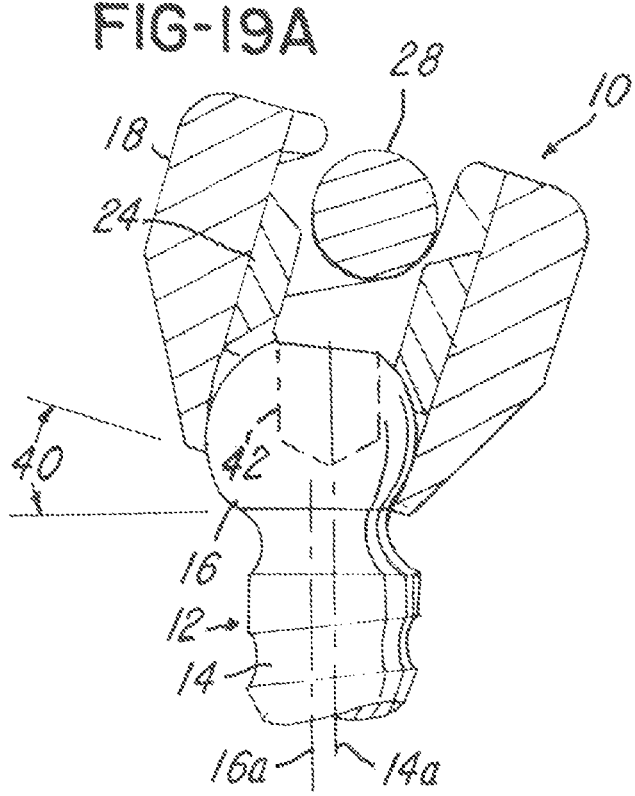
FIGS. 19A and 19B are enlarged, partial sectional views of the polyaxial screw assembly depicted in FIG. 16, wherein the compression member and rod in unlocked and locked positions and the retainer has been pivoted to a maximum degree in a second direction.
Figure 19B:
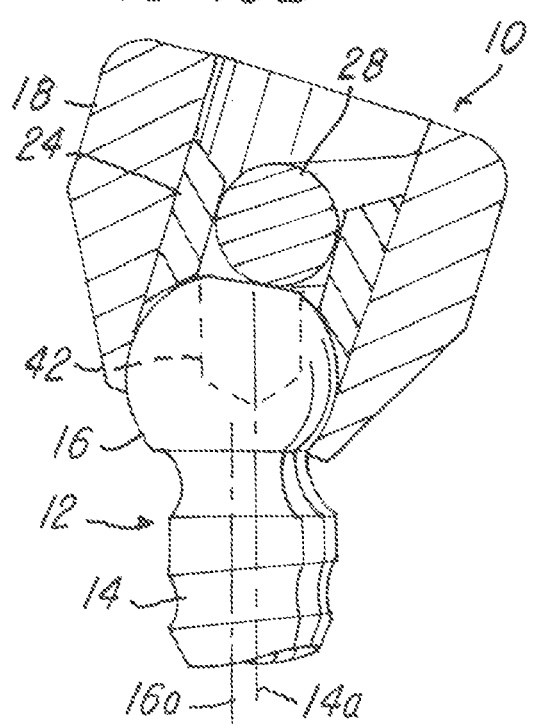
Figure 20:
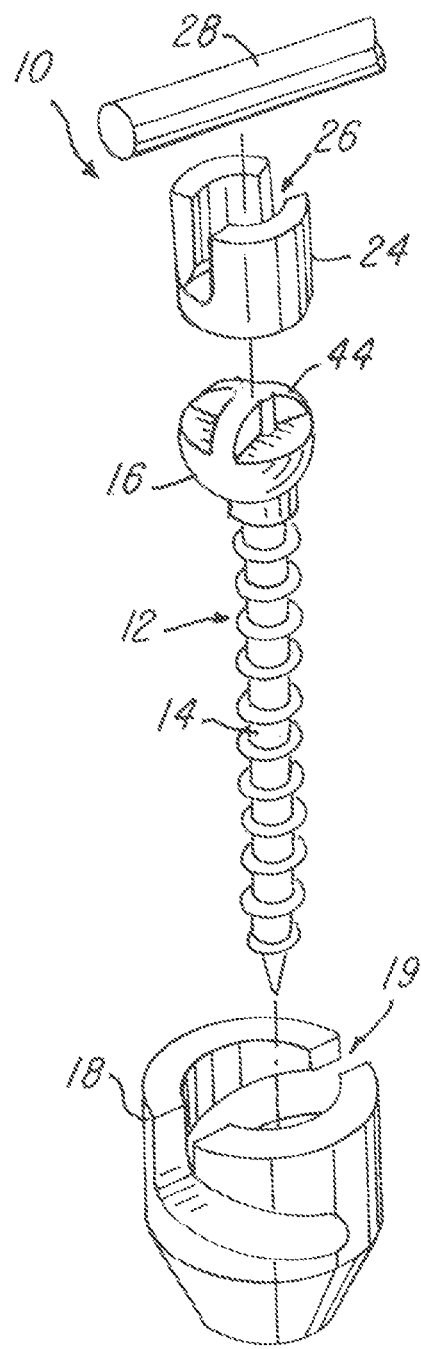
FIG. 20 is an exploded perspective view of a polyaxial screw assembly having a second alternative configuration, wherein a compression member and a rod for engagement with the compression member are also shown.
Figure 21:
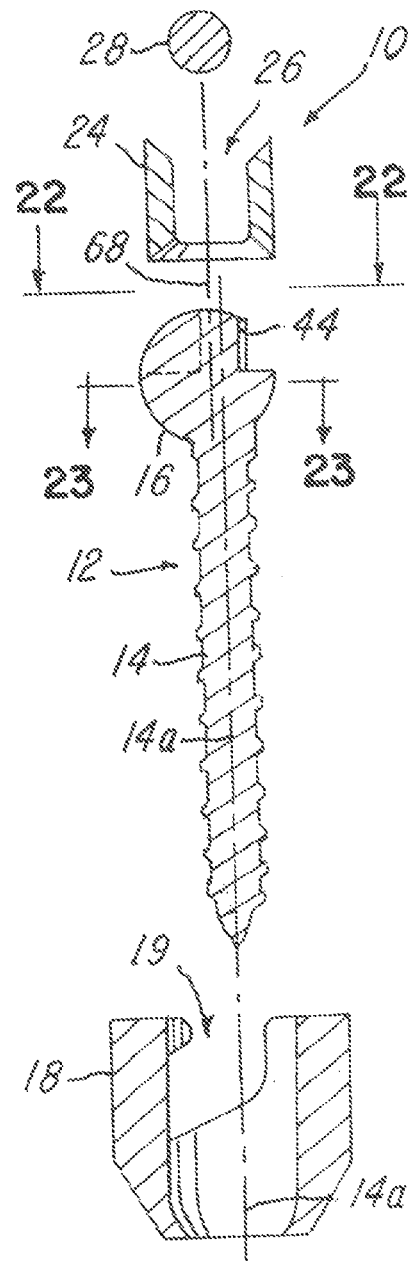
FIG. 21 is an exploded side view of the polyaxial screw assembly depicted in FIG. 20.
Figure 22:
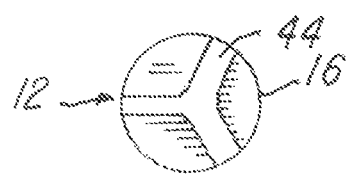
FIG. 22 is a top view of the polyaxial screw assembly depicted in FIGS. 20 and 21 taken along line 22-22 in FIG. 21.
Figure 23:
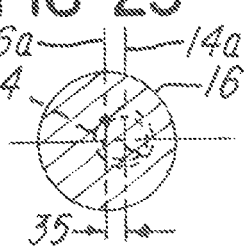
FIG. 23 is a top sectional view of the polyaxial screw assembly depicted in FIGS. 20 and 21 taken along line 23-23 in FIG. 21.

FIG. 11B shows the rod 28 in a loaded and locked position after the retainer 18 has been pivoted and rotated to the locked position.

It will be understood that the partial opening or partial shape of the screw head 16 and the corresponding tool or driver utilized to interface therewith may take any desirable form. Besides the exemplary slots 30 and tool 34 shown in FIGS. 6, 8 and 9, other possible configurations of the screw head 16 include, but are not limited to a shape adapted to define a hexagonal opening 42 (FIGS. 14 and 17), a "Y" shape 44 (FIGS. 22 and 25), and an opening 46 defined by a plurality of side walls (FIGS. 30 and 33). Of course, corresponding tools 48 (FIG. 16), 50 (FIG. 24) and 52 (FIG. 32) would be utilized therewith, respectively. It will be appreciated that the respective tool may have a linear configuration (as evidenced by tools 34 and 48) or a non-linear configuration (as seen for tools 50 and 52).

Moreover, the embodiments of FIGS. 4-35B illustrate use of the screw 12 with the compression module 17, but it should be understood that the screw 12 may be used with retainers that do not utilize a compression module 17. It should be understood that while the embodiments illustrated in FIGS. 4-35B illustrate the use of the screw 12 with a capless retainer and compression module 17, the screw 12 may be used with non-capless systems. For example, FIGS. 36 and 37 illustrate the use of the screw 12 with a non-capless retainer 18'. In this embodiment, retainer 18' has a threaded interior surface for receiving a threaded cap 39. Of course, the screw 12 may also be used with other types of retainers that utilize other means for retaining the rod in the receiver, and such receivers and securing mechanisms are known to those skilled in the art.

Referring now to FIGS. 38-44, another embodiment is shown. In this embodiment, those parts that are the same or similar to the part shown in FIGS. 4-35B are identified with the same part number.

Figure 41:
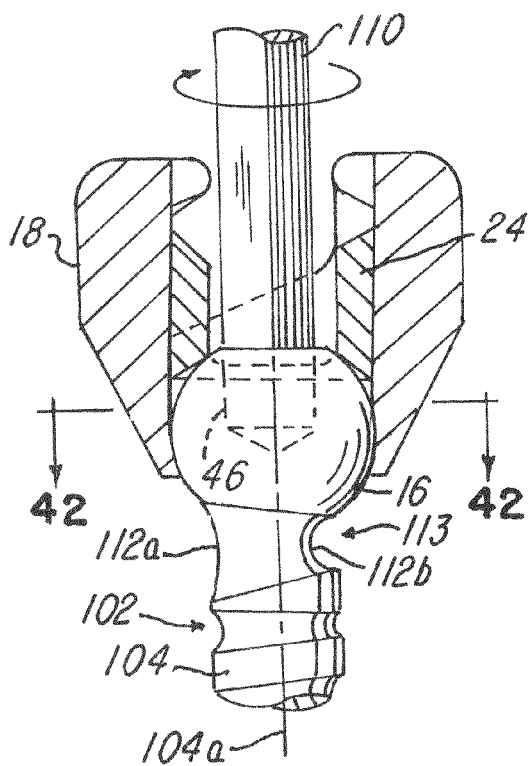
FIG. 41 is a fragmentary sectional view of the embodiment shown in FIG. 39 illustrating the use of a tool that becomes coaxial with the axes and shank.

As shown in FIGS. 38 and 39, notice that this embodiment utilizes a screw 102 having a threaded shank 104 and a head 106. The head 106 comprises a female aperture 108 for receiving a tool for screwing the screw 102. In the illustration being described, and as illustrated in FIG. 41, the tool 110 may be a linear tool, without an offset of the type illustrated in FIG. 24, for example. Notice that in this embodiment, the receiver 18 comprises an axis 112 that is coaxial with the axis 104a of the shank 104. Notice also that the head 106 comprises an axis 106a that is coaxial with both the axis 104a of shank 104 and the axis 112 as illustrated in FIG. 39. This is advantageous in that when the screw 102 is rotatably driven, it may be driven along a common axis which facilitates mounting or screwing the screw 102 into bone.

As best illustrated in FIGS. 38 and 39, notice that the head 106 is integrally secured to the shank 104 by an intermediate or neck portion 113. As shown in FIGS. 41-43 and 44, notice that the neck portion 113 comprises a first surface or area 112a having a relatively large radius and a second surface or area 112b that has a relative small radius as shown. The larger and small radiuses of the surfaces 112a and 112b permit the retainer 18 to be pivoted a plurality of different angles or degrees. For example, FIG. 43 illustrates the retainer 18 pivoting to the left (as viewed in FIG. 43) a predetermined angle 114 as shown. In contrast, notice in FIG. 44, the relatively small radius surface 112b defines an area or intermediate portion 113 that permits the retainer 18 to pivot toward the right (as viewed in FIG. 44) a predetermined angle 116 which is greater than the predetermined angle 114 as in at least one area of the intermediate portion 113.

To enable the polyaxial movement, notice in FIG. 41 that the intermediate portion 113 is neither centric nor symmetrical about the axis 104a. Thus, the intermediate portion 113 is eccentric about axis 104a. Notice in FIGS. 38-45 that the radius of curvature is not constant about the axis 104a and generally becomes larger as the radius of curvature moves from the portion or area 112b toward the area 112a, with the area 112a having the largest radius of curvature. Thus, not only is the intermediate portion 113 not symmetrical about the axis 104a, but the radius of curvature changes as well.

This embodiment enables the system of FIGS. 38-45 to enable the retainer 18 to pivot a plurality of angles about the head 106, with the greatest degree of pivot being realized when the retainer 18 pivots toward the smallest radius of curvature 112b and the smallest amount of pivot being achieved when the retainer 18 is pivoted toward the largest radius of curvature 112a. Thus, the embodiment of FIGS. 38-45 enables the retainer 18 to pivot a plurality of different angles about the head 106 as shown.

Figure 24:
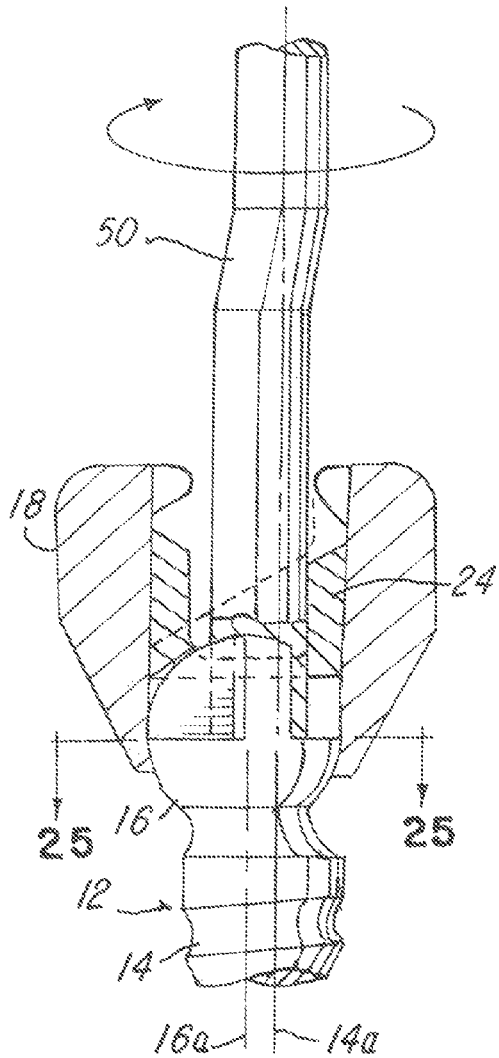
FIG. 24 is an enlarged, partial sectional view of the polyaxial screw assembly depicted in FIGS. 20 and 21, wherein a tool is shown as interfacing with a head portion thereof to position it within the retainer.
Figure 25:
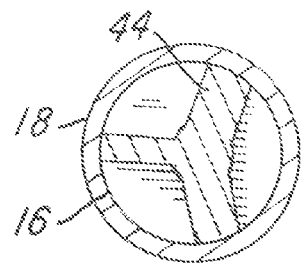
FIG. 25 is a top section view of the polyaxial screw assembly with the head portion thereof positioned within the retainer, as depicted in FIG. 24, taken along line 25-25 of FIG. 24.
Figure 26:
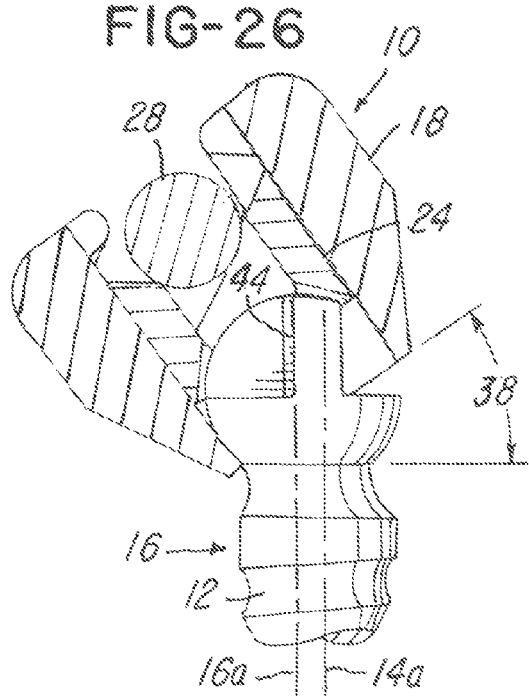
FIG. 26 is an enlarged, partial sectional view of the polyaxial screw assembly depicted in FIG. 24, wherein the compression member and rod engaged therewith are included and the retainer has been pivoted to a maximum degree in a first direction.
Figure 27A:
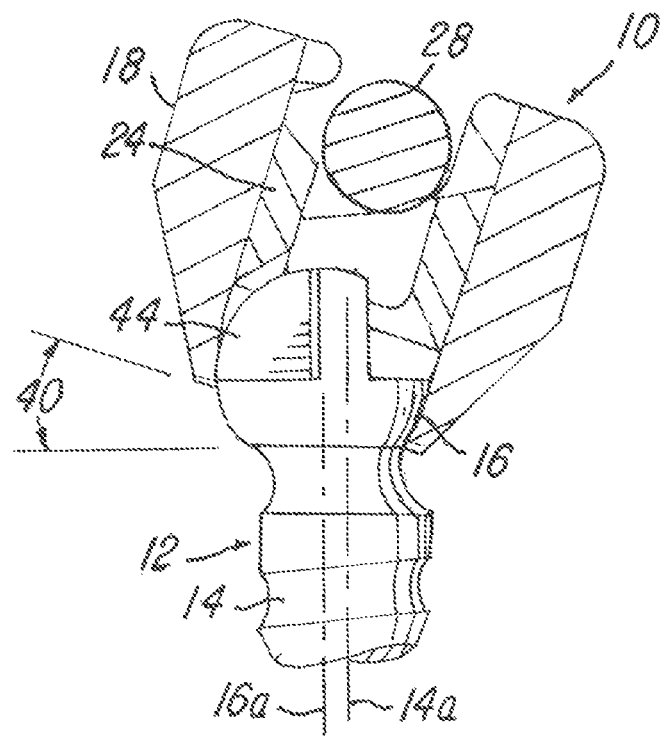
FIGS. 27A and 27B are enlarged, partial sectional views of the polyaxial screw assembly depicted in FIG. 24, wherein the compression member and rod in unlocked and locked positions.
Figure 27B:
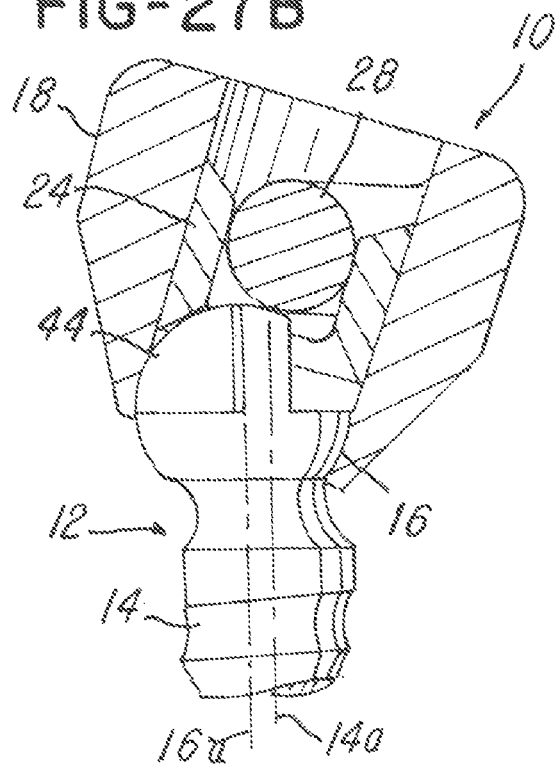
Figure 35B:
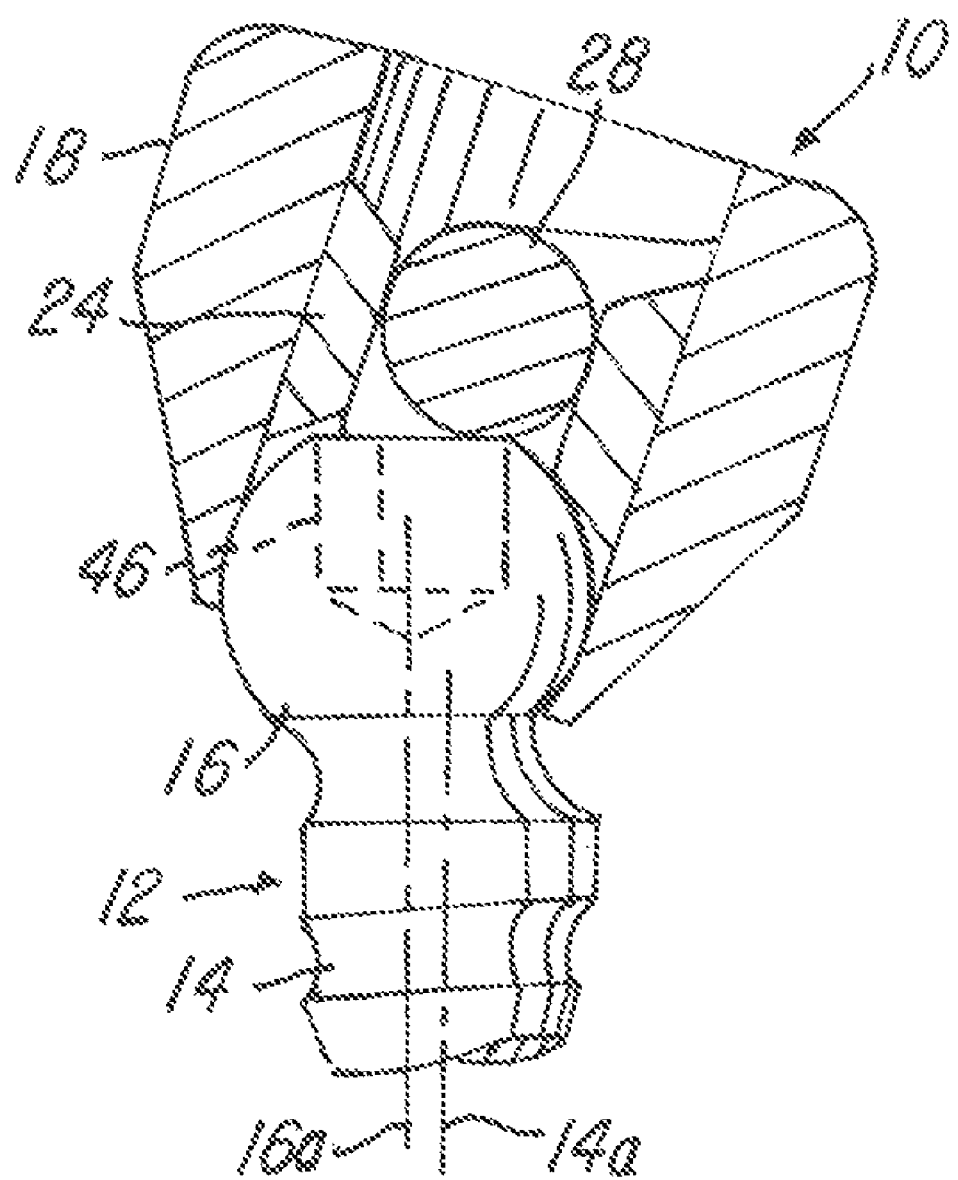

Another advantage of the embodiment illustrated in FIGS. 38-44 is that it enables the use of the tool 110 that is generally linear and that is not offset as illustrated, for example, in the embodiment shown in FIG. 24. This facilitates enabling the tool 110 to become coaxial with the axes of the head 106 and shank 104, as illustrated in FIG. 41, which facilitates rotating the screw 102 and mounting in into bone.

Figure 42:
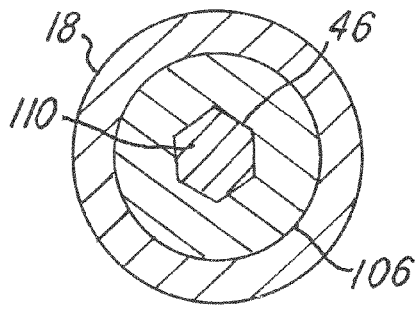
FIG. 42 is a sectional view taken along the line 42-42 in FIG. 41.
Figure 43:
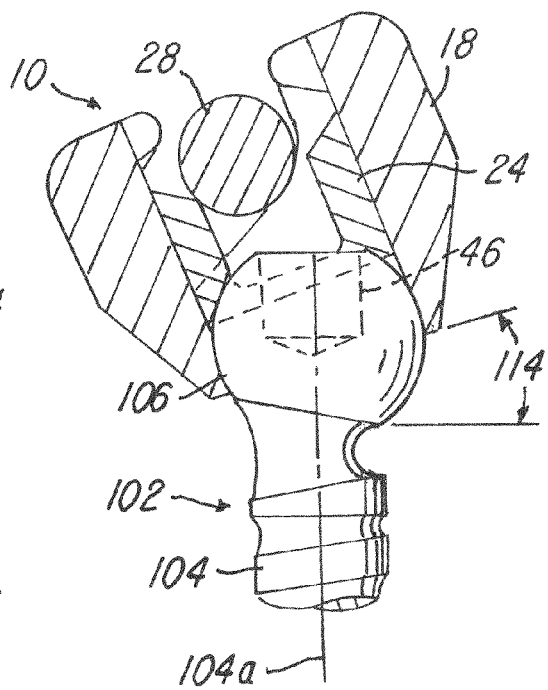
FIG. 43 is a fragmentary sectional view of the embodiment shown in FIG. 38 illustrating the pivotal movement of the retainer relative to the head, with the retainer being in an unlocked position.
Figure 44:
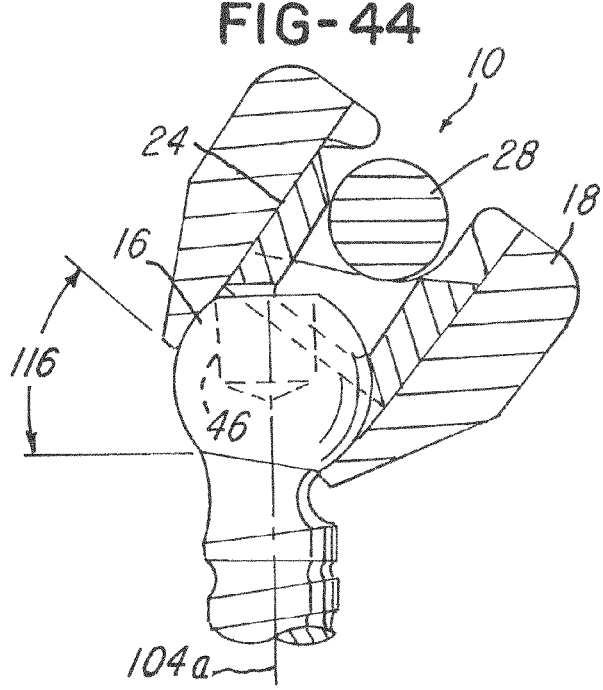
FIG. 44 is another fragmentary sectional view of the embodiment shown in FIG. 38 illustrating the pivotal movement of the head in a direction that is different from the direction shown in FIG. 43, but illustrating a greater degree of pivoting.

FIG. 42 shows a cross-section of the illustration shown in FIG. 41 illustrating the tool 110 being coaxial with the head 106 as shown.

Note also that an intersection of the screw head 16 to the threaded portion 14 may have a wall 14b (FIGS. 5 and 8) that defines an area 14c that is generally concave and permits a bottom edge 18a1 (FIGS. 4, 5 and 8) of retainer 18 to move inwardly toward centerline axis 14a and inside an imaginary plane defined by the outside edge 14d (FIG. 8) of at least one thread on the threaded portion 14.

Having shown and described the preferred embodiment of the present invention, further adaptations of the capless multiaxial screw can be accomplished by appropriate modifications by one of ordinary skill in the art without departing from the scope of the invention.

While the system and method herein described constitute preferred embodiments of this invention, it is to be understood that the invention is not limited to this precise system and method, and that changes may be made therein without departing from the scope of the invention which is defined in the appended claims.

What is claimed is:

1. A multiaxial screw fixation system, comprising:
    (a) a screw having a threaded portion and a screw head portion positioned at one end thereof; said threaded portion having a first centerline axis extending therethrough and said screw head portion having a second centerline axis extending therethrough, wherein said first centerline axis and said second centerline axis are not co-axial; and
    (b) a retainer having a first end, a second end opposite said first end, and a bore for receiving said threaded portion so that said screw head portion may be seated therein;
    wherein said screw is adapted such that said retainer is able to pivot about said screw head portion in a non-symmetrical manner;
    said screw being adapted to permit said retainer to pivot on said screw such that an angle of movement of said retainer relative to said second centerline axis of said screw head portion is greater in a first direction compared to movement of said retainer in a second direction that is opposite said first direction; and
    wherein said screw comprises an intermediate portion between said screw head portion and said threaded portion; said intermediate portion being non-symmetrical about said first centerline axis.

2. The multiaxial screw fixation system of claim 1, wherein said second direction is opposite of said first direction.

3. The multiaxial screw fixation system of claim 1, wherein said retainer is a capless retainer.

4. The multiaxial screw fixation system of claim 1, wherein said retainer comprises a cap for retaining a rod in the retainer.

5. The multiaxial screw fixation system of claim 1, wherein a centerline axis through said screw is co-linear with a centerline axis of said retainer.

6. The multiaxial screw fixation system of claim 1, wherein said screw head portion is not symmetrical with respect to said first centerline axis of said threaded portion.

7. The multiaxial screw fixation system of claim 1, said screw head portion further comprising a partial opening formed therein for receiving a corresponding tool.

8. The multiaxial screw fixation system of claim 7, wherein a centerpoint of said partial opening is offset from said second centerline axis of said screw head portion.

9. The multiaxial screw fixation system of claim 7, wherein a centerpoint of said partial opening is aligned with a first centerline axis of said threaded portion.

10. The multiaxial screw fixation system of claim 7, wherein said partial opening is a pair of intersecting slots.

11. The multiaxial screw fixation system of claim 7, wherein said partial opening is at least one of a hexagonal opening or a y-shaped slot.

12. The multiaxial screw fixation system of claim 1, wherein said second centerline axis through said screw head portion is offset from said first centerline axis of said threaded portion.

13. The multiaxial screw fixation system of claim 1, wherein said second centerline axis of said screw head portion is oriented at an angle to said first centerline axis of said threaded portion.

14. The multiaxial screw fixation system of claim 1, wherein said intermediate portion comprises a radius of curvature that changes about an axis of the threaded portion.

15. The multiaxial screw fixation system of claim 14, wherein said screw head portion and said threaded portion comprise a common axis, said intermediate portion being non-symmetrical or non-concentric about the common axis.

16. The multiaxial screw fixation system of claim 1, said retainer including a receiving channel for receiving an elongated member.

17. The multiaxial screw fixation system of claim 1, further comprising a compression member for situating in said bore and engaging said screw head portion.

18. A multiaxial screw fixation system comprising:
(a) a screw, further comprising:
(1) a threaded portion having a centerline axis extending therethrough; and
(2) a head portion positioned at one end of said threaded portion, said head portion having a centerline axis extending therethrough, wherein said threaded portion centerline axis and said head portion centerline axis are not co-axial;
(b) a retainer having a first end, a second end opposite said first end, a centerline axis extending therethrough, and a bore for receiving said threaded portion so that said head portion is seated therein;
wherein said retainer is able to pivot about an axis of said threaded portion in a non-symmetrical manner; and
wherein said screw comprises an intermediate portion between said head portion and said threaded portion; said intermediate portion being non-symmetrical about said threaded portion centerline axis.

19. A polyaxial screw for use during a surgical procedure, said polyaxial screw comprising:
a threaded shank having a shank axis, wherein said shank axis extends through a centerline of said threaded shank; and
a head having a head axis, wherein said head axis extends through a centerline of said head;
wherein said head is integral with said threaded shank, said head being adapted to permit a retainer to pivot or move about said head axis,
wherein said head axis is offset from said shank axis;
wherein said head axis and said shank axis are not co-axial; and
wherein said polyaxial screw comprises an intermediate portion between said head and said threaded shank; said intermediate portion being non-symmetrical about said shank axis.

20. The polyaxial screw as recited in claim 19, wherein said head is generally spherical and comprises at least one recessed area adapted to receive a tool for rotating said polyaxial screw.

21. The polyaxial screw as recited in claim 20, wherein said at least one recessed area comprises a plurality of recessed areas.

22. The polyaxial screw as recited in claim 20, wherein said at least one recessed area comprises a plurality of recessed areas defines a y-shaped engaging area or a plurality of non-intersecting recessed areas.

23. The polyaxial screw as recited in claim 19, wherein said threaded shank has a wall defining a recessed area to permit an end of said retainer to pivot toward said shank axis and inside an imaginary line defined by an outside edge of at least one thread of said threaded shank.

24. The polyaxial screw as recited in claim 19, wherein said intermediate portion comprises a radius of curvature that changes about the axis.

25. A polyaxial screw for use during a surgical procedure, said polyaxial screw comprising:
a threaded shank having a shank axis, wherein said shank axis extends through a centerline of said threaded shank;
a head having a head axis, wherein said head axis extends through a centerline of said head; and
an intermediate portion integrally coupling said threaded shank to said head;
said intermediate portion and said threaded shank having a common axis and being centric or non-symmetrical about said shank axis;
wherein said head axis and said shank axis are not co-axial.

* * * * *